(12) United States Patent
Li et al.

(10) Patent No.: US 7,897,820 B2
(45) Date of Patent: Mar. 1, 2011

(54) PROCESS FOR PREPARING ERIANIN

(75) Inventors: Yiping Li, Taizhou (CN); Shuangxi Liu, Taizhou (CN)

(73) Assignee: Zhe Jiang Cell Biomedical Research Co., Ltd., Taizhou, Zhejiang Province (CN)

( * ) Notice: Subject to any disclaimer, the term of this patent is extended or adjusted under 35 U.S.C. 154(b) by 400 days.

(21) Appl. No.: 11/995,672

(22) PCT Filed: Jul. 12, 2006

(86) PCT No.: PCT/CN2006/001649

§ 371 (c)(1), (2), (4) Date: Aug. 15, 2008

(87) PCT Pub. No.: WO2007/006230

PCT Pub. Date: Jan. 18, 2007

(65) Prior Publication Data

US 2009/0018369 A1  Jan. 15, 2009

(30) Foreign Application Priority Data

Jul. 13, 2005 (CN) .................... 2005 1 0083055

(51) Int. Cl.
*C07C 41/18* (2006.01)
(52) U.S. Cl. .................... 568/644; 568/13; 568/16; 568/17; 568/315; 568/316
(58) Field of Classification Search ........ None
See application file for complete search history.

(56) References Cited

U.S. PATENT DOCUMENTS

| 5,430,062 A | 7/1995 | Cushman et al. ............ 514/646 |
| 6,759,555 B2 | 7/2004 | Mutti et al. ................. 564/193 |

FOREIGN PATENT DOCUMENTS

| CN | 1660745 A | 8/2005 |
| CN | 1704393 A | 12/2005 |

OTHER PUBLICATIONS

Machine generated translation of CN 1704393, published Dec. 2005.*

Getahun, Z. et al., "Synthesis of alkoxy-substituted diaryl compounds and correlation of ring separation with inhibition of tubulin polymerization: differential enhancement of inhibitory effects under suboptimal polymerization reaction conditions", Journal of Medical Chemistry, 35(6); 1992, pp. 1058-1067.

* cited by examiner

*Primary Examiner*—Rosalynd Keys
(74) *Attorney, Agent, or Firm*—Greer, Burns & Crain, Ltd.

(57) ABSTRACT

A process for preparing Erianin (Dihydro Combretastation A-4), wherein 3,4,5-trimethoxy benzaldehyde is converted to phosphonium salt or phosphonate ester or the likes thereof, then reacted with isovanillin (3-hydroxyl-4-methoxyl benzaldehyde) including a protected hydroxyl in the 3-position, followed by hydrogenation and deprotection.

11 Claims, 6 Drawing Sheets

```
                              Area Percent Report

Data File : C:\HPCHEM\1\DATA\20050708.D                    Vial: 5
Acq On    : 8 Jul 2005 15:10                           Operator:
Sample    :                                                Inst : GC/MS Ins
Misc      :                                            Multiplr: 1.00
                                                  Sample Amount: 0.00
MS Integration Params: rteint.p Method    : C:\HPCHEM\1\METHODS\HE-2003.M (RTE Integrator)
Title     :
Smoothing : ON                                      Filtering: 5
Sampling  : 1                                        Min Area: 0.5 % of largest Peak
Start Thrs: 0.2                                     Max Peaks: 100
Stop Thrs : 0                                   Peak Location: TOP If leading or trailing edge < 100 prefer < Baseline drop else tangent >
Peak separation: 5

Signal    : TIC peak  R.T. first max last  PK   peak      corr.     corr.    % of
 #    min  scan scan scan  TY   height    area      % max.   total
---  ----- ---- ---- ---- ---- --------- --------- -------- -------
 1  12.744 1694 1710 1774 rBV  13659146  44053939  100.00%  98.022%
 2  13.285 1793 1801 1816 rVB    454428    889039    2.02%   1.978%

Sum of corrected areas:    44942978

20050708.D  HE-2003.M    Fri Jul 08 15:27:13 2005
```

FIG. 5

PROCESS FOR PREPARING ERIANIN

FIELD OF THE INVENTION

The present invention relates to a process for preparing Erianin.

BACKGROUND OF THE INVENTION

Cancer is considered to be the worst disease except the cardiovascular disease. At present chemotherapy and radiotherapy are frequently used for treatment of cancer, but their toxicant and side effect is very adverse for health. The specialists home and abroad have found that dendrobium, a kind of traditional Chinese medicine, can be antineoplastic, anti-aging and expanding blood vessel, and its extract by ethanol and the bibenzyl compounds have antineoplastic activity in vivo of different degrees. The active component of dendrobium has caught the attention of the world.

The findings of Wang Tianshan (In vitro Inhibition Activities on the Growth of Tumor Cell Strain K256 by Constituents from Dendrobium Chrysotoxum, *Natural Product Research and Development*, 1997, 9 (2), 1~3) showed that bibenzyls and phenanthrenes have inhibitory effect on the assembling and caryocinesis of the in vitro cultured murine microtubulin $L_{1210}$, $P_{388}$ cell strain and many human tumor cell strains including A-549, MCF-7, HT-29, SKMEL-5, MLM, SK-OV-3, and HL-60. The dihydrobibenzyls and phenanthrenes in Dendrobium chrysotoxum have different degrees of inhibitory effect on the growth of tumor cell strain $K_{256}$, among which Erianin (dihydrocombretastatin A-4) is the most active.

Erianin has the best effect on the liver cancer of mouse, its tumor inhibitory rate being 50.82%. Related study (*Inhibitory effects of dendrobium chrysotoxum and its constituents on the mouse HePA and ESC, Journal of China Pharmaceutical University*, 1994, 25 (3), 188~189) infers that the side effect of Erianin is far lower then 5FU, the medicine for chemotherapeutics of cancer. Erianin have negative proton effect to many kinds of cancer cells, the effecting target being the microtubulin in the cell. It can inhibit the polymerizing of microtubulin, stimulate the hydrolization of microtubulin-dependent GTP, and competitively bind with protein with colchicine. The study of Li Yunman (*Erianin Induces Apoptosis of Human leukemia HL-60 cells*, Acta Pharmacologica Sinica, 2001, November, 22(11), 1018-1022) showed that Erianin significantly inhibited the growth of human leukemia HL-60 cells. The inhibition might be the result of the induced apoptosis and the altered expression of bcl-2 and bax genes in HL-60 cells.

The chemical name of Erianin is 2-methoxyl-5-[2-(3,4,5-trimethoxy phenyl)]ethyl phenol, its molecular formula being $C_{18}H_{22}O_5$ and molecular weight being 318.35, and its chemical structural formula is as follows:

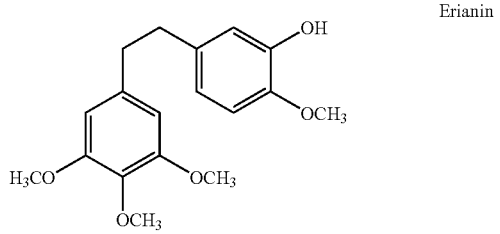

Erianin

At present, the preparative process of Erianin is extracting Erianin from dendrobium by separating and extractive technique of Chinese materia medica. The Chinese patent application CN03115752.1 disclosed the method of extracting Erianin from dendrobium, comprising extraction by supercritical $CO_2$ and column chromatography using absolute alcohol, methanol, acetone as entrainer to extract Erianin, the antineoplastic active component, from orchidaceae plants, dendrobium, using $CO_2$ as extracting medium; The crude extract was chromatographed by a silica column using an eluting reagent of petroleum benzene: ethyl acetate solution, and recrystallizing to get the refined extractive.

As this method is of high technical specification, and the source of dendrobium is scarce, it is not suitable for mass production.

In addition, previous literature (*Synthesis of Stilbene and Dihydrostilbene Derivatives and Their Value as Potential Anticancer Agents That Inhibit Tubulin Polymerization, Mark Cushman. J. Med. Chem.* 1991, 34, 2579-2588,) dealt with the synthesis of stilbene and dihydrostilbene derivatives, but the method for synthesis of Erianin was not involved in particularly. It neither described the synthesizing technology and yield of the intermediate. Silyloxylated was used as phenolic hydroxyl protecting group in the article, but benzyl group is used in present invention, for the reactions of deprotection and hydrogenation can be completed at the same time, which is more simple to implement, and fit for industrial production. Besides, there was sodium hydride and sodium methylate in the Wittig reaction in above articles, but in the present invention, sodium tertiary butoxide is used, which can be more stabilization and easier to react.

In the literature concerned with the synthesizing of Erianin (*Synthesis of Alkoxy-Substituted Diaryl Compounds and Correlation of Ring Separation with Inhibition of Tubulin Polymerization: Differential Enhancement of Inhibitory Effects under Suboptimal Polymerization Reaction Conditions, J. Med. Chem.* 1992, 35, 1058-1067 *Zelleka Getahun*), the starting material for reaction was different from present invention. 3,4,5-trimethoxybenzaldehyde and isovanillin used in the present invention are common in the material market and cheap. They can be bought or produced by oneself, so as to avoid significant influence on the cost of the product caused by the change in the cost of material. According to the literature, the intermediate, cis-trans-isomer, went on for further reaction without crystallization, which was disadvantageous for the next procedure and the calculation of the yield of the product. In this invention, the cis-trans-isomer is crystallized before the next step, which would facilitate batch feeding, lower the cost and increase the yield (80.48%, as against 72% in the literature). According to the literature, there must be a step of purification by column after the hydrogen reduction reaction, so the efficiency was low. But in present invention, recrystallisation is done directly to remove benzyl-chlorination which is a coproduct in the solution. The operation is simple, advanced, and efficient, fit for industrialized production. No high vacuum distillation or reaction under high temperature and high pressure that asks for rigorous production condition but is of low yield is required in this invention. In present invention, the reaction condition is moderate, and there is no complicated but inefficient operation such as column chromatography, so the yields in every step can be controlled above 80%, both the single-step yield and overall yield being very high.

In the process of the synthesis of Combretastatin (*Isolation and Synthesis of Antineoplastic Agents 291 Combretastatins A-4, A-5, and A-6, J. Med. Chem.* 1995, 38, 1666-1672, George R. Pettit), the synthetic route of CA4, the intermedium of Erianin, was described, in which the phenolic hydroxyl protecting group was silyloxylated. In present invention, benzyl group is used for the direct deprotection in hydrogenation reaction. In the above article, there is sodium n-butoxide in the Wittig reaction, but present invention use potassium t-butoxide which is cheaper, safer, and easier to operate.

SUMMARY OF THE INVENTION

The present invention is to provide a process for preparing Erianin, and it is the first time to prepare Erianin by synthetic method. Its raw material is easy to get and the reagents used are cheap, it is fit for industrialized mass production.

There is provided, in accordance with the present invention, a process for preparing Erianin, comprising follow steps:

A1. Bonding reaction: compound (I) was reacted with compound (II) in the inert solvent which contain alkali to form compound (III);

A2. Hydrogenation reaction: reacting compound (III) obtained in step A1 was reacted with hydrogen in organic solvent, by using an hydrogenation catalyst to form compound (IV);

A3. Hydroxy group deprotection reaction: removing the hydroxyl protecting group R of compound (IV) obtained in step A2 to form Erianin;

wherein,

X is halogen selected from a group consisting of Cl, Br, or I, and Br is the preferred;

R is phenolic hydroxyl group selected from a group consisting of benzyl group, tetrahydropyrane, acetyl group, and tert-butyl. Describing above listed are good as some of the fine protecting groups, besides, and there are many other groups that can be used as phenolic hydroxyl group for protection. And as benzyl group is more convenient for deprotection, so it is currently preferred that R is preferably benzyl group in the present invention.

The synthetic route is:

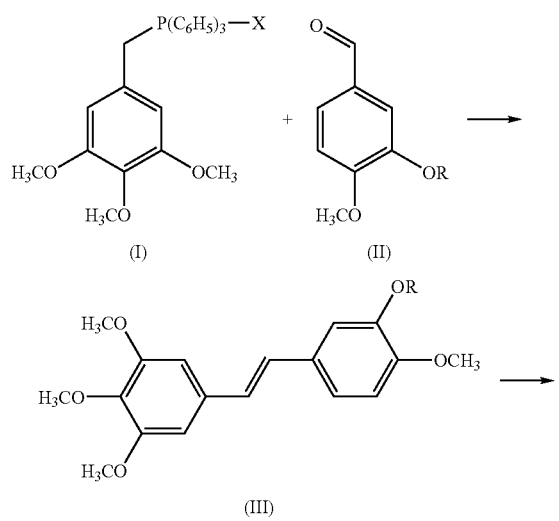

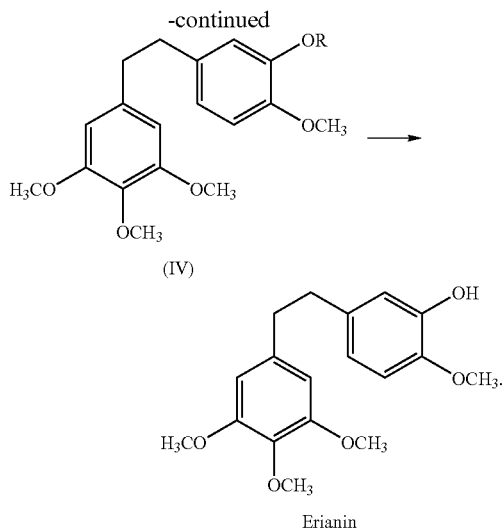

Erianin

In above synthetic route, compound (I) is 3,4,5-trimethoxyl benzyl-triphenylphosphine bromide. compound (II) is isovanillin, whose hydroxy group is protected, and compound (III) is cis-trans-isomer.

Where in Step A1:

The inert solvent for the reaction is one or more kinds of solvent selected from a group consisting of dioxane, tetrahydrofuran, dimethylformamide, dimethyl sulphoxide, acetonitrile, hexamethyl phosphoramide or tetrachlormethane; in which tetrahydrofuran is preferred.

The alkali used can be all kinds of organic alkalis or inorganic alkalis. For example, $Na_2CO_3$, $K_2CO_3$, NaH, KH, or other similar inorganic alkalis; potassium t-butoxide, pyrimidine, various dimethylpyridine, 4-dimethyl amino pyridine, triethylamine, diisopropylethylamine, or other similar organic alkalis. The preferred organic alkalis are potassium t-butoxide, triethylamine, diisopropylethylamine. Potassium t-butoxide was used as the alkali preferably for the reaction in one embodiment of the invention.

In one preferred embodiment of this present invention, after stirring the bonding reaction mixture at room temperature for 5 minutes, cooling it in refrigeratory. Compound (II) was added dropwise and slowly for 20 minutes, then stirring for another 30 minutes at room temperature. After the completion of the reaction, extracting with diethyl ether, drying, filtering, concentrating to get oily product, adding absolute alcohol to solidify, and suction filtering to get faint yellow solid. Then dissolving with anhydrous alcohol when heated, stirring at room temperature, suction filtering, washing and drying by infrared lamp to get the pure C is/Trans Product (III), a kind of faint yellow powder.

Where in Step A2:

The said organic solvents of the present invention is one or more kinds of solvents selected from group consisting of aromatic hydrocarbons, ketones, esters and alcohols. The solvent of aromatic hydrocarbons includes benzene, toluene, xylene, and styrene; the solvent of ketones includes acetone, cyclohexanone, and methylethylketone; the solvent of esters includes ethyl acetate, buty lacetate, and isovaleric methyl ester; and the solvent of alcohols includes methanol, ethanol, butanol, and isopropyl alcohol.

In step A2, the organic solvent is selected from at least one of esters or alcohols, the preferred one being the mixed solvent of ethyl acetate and ethanol.

Hydrogenation catalyst is selected from at least one of palladium or nickel series, such as Pd—C catalyst and Ni—Al-catalyst. In one example of the invention, Pd—C catalyst is preferred.

Where in Step A3:

R is benzyl group as preferred, and the protecting group can be removed during the hydrogenation reaction in step A2. The protecting group can be removed by the common practice in the field to get Erianin if other phenolic hydroxyl protecting group such as tetrahydropyran is used.

In one preferred embodiment of the present invention, dissolving compound (III) with R being benzyl group in the mixture of ethyl acetate and absolute alcohol in the hydrogenation reaction to get a faint yellow solution, adding 5% Pd—C, stirring while inputting hydrogen, stirring for 3 hours at room temperature, filtering, concentrating to get oily product, the crude product of compound (I). Dissolving the crude product in anhydrous alcohol, filtering and standing at room temperature, and crystal is separated. Leaving it overnight, filtering, and washing the filter cake with ether to get white crystal of Erianin.

Further according to the common practice in the field, above compound (I) can be made by 3,4,5-trimethoxybenzaldehyde or 3,4,5-trimethoxyl toluene.

When starting material is 3,4,5-trimethoxybenzaldehyde, the synthetic method comprises following steps:

(a) preparing compound (VI) from compound (V) in the presence of reducing agent;

(b) reacting compound (VI) with halide to form compound (VII);

(c) reacting compound (VII) with triphenylphosphine to form compound (I) the synthetic route is:

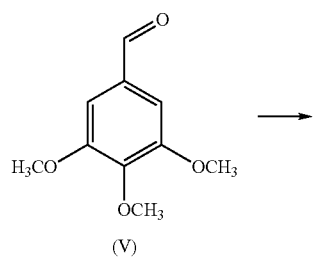

(V)

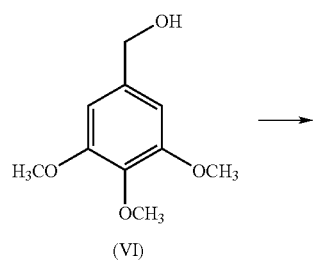

(VI)

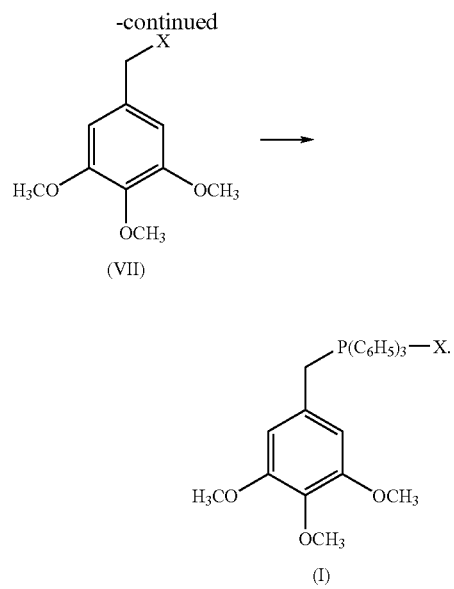

In step c, ethylphosphine can take the place of triphenylphosphine in the reaction to form Erianin.

In one specific embodiment of the present invention: in step a, dissolving compound (V) in anhydrous alcohol when heated at 40(±5)° C., then adding sodium borohydride and heating to reflux; after the completion of the reaction, quenching with deionized water, washing with anhydrous alcohol and sodium hydroxide solution, drying by anhydrous magnesium sulfate overnight, and concentrating in rotarory evaporater till it is dried to obtain the colorless oily compound (VI), which can be purified by vacuum distillation. In step b, dissolving phosphorus tribromide in dichlormethane partes aequales, slowly adding it dropwise to the solution of dichlormethane dissolved with compound (VI), and leaving it to react at room temperature for 50 minutes. Then cooling the solution in refrigeratory, washing, concentrating, drying, recrystallizing with a 1:3 mixture of ethyl acetate and n-hexane to get the white lamellar crystal (VII). In step c, adding triphenylphosphine to compound (VII), dissolving immediately, heating to reflux, suction filtering, and vacuum drying to get 3,4,5-trimethoxyl benzyl triphenylphosphine bromide (I). Pure product of white powder solid is obtained after washed with acetone.

In another preferred embodiment of this invention, the method of bromination of 3,4,5-trimethoxyl toluene is used to get compound (VII).

Compound (II) was obtained by protecting the hydroxyl group of isovanillin (VIII) by method of esterification or etherification, the preferred group used to protect is benzyl group.

If benzyl group is used, the deprotection can be completed during the hydrogenation reaction. If tetrahydropyrane is used, the deprotection can be done using the routine method in the field to get the final product Erianin.

Furthermore, when R of compound (II) was benzyl group, it was compound (X), the hydroxyl group of isovanillin (VIII) was protected with benzyl group. It can be prepared in the following synthetic route:

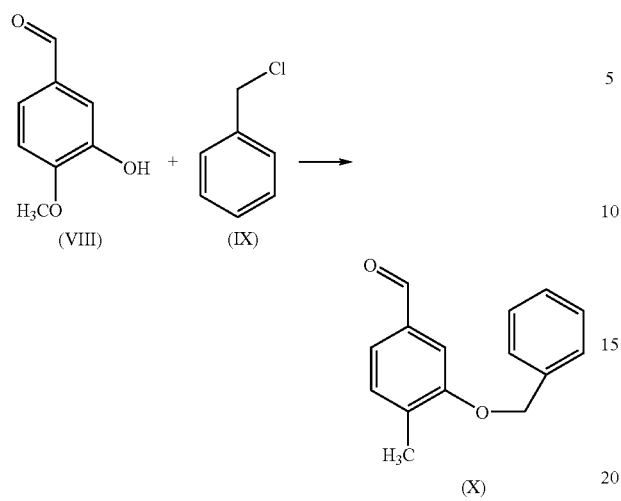

In one preferred embodiment of this invention, heating isovanillin to 40° C., adding potassium carbonate, then adding benzylchloride (IX) under stirring, and was heated to reflux. When the reaction was completed, cooling it to 50° C., filtering while hot, then cooling the filtrate in refrigeratory overnight, and the crystal was precipitated; after suction filtering and vacuum drying to get compound (X) of white needlelike crystal. Recrystallisation with absolute alcohol can get white styloid crystal.

The present invention also provides another process for preparing Erianin, comprising following steps:

(B1) reacting compound (VII) with triethyl phosphite ($(C_2H_5O)_3P$) in the aromatic organic solvent to form compound (XI);

(B2) reacting compound (XI) with compound (II) in the inert solvent which contains alkali to form compound (III);

(B3) hydrogenating compound (III) was reacted with hydrogen to form compound (IV) in organic solvent with hydrogenation catalyst;

(B4) removing the hydroxyl protecting group R of compound (IV) from step (B3) to form Erianin;

wherein,

X is halogen selected from a group consisting of Cl, Br, and I and Br is preferred.

R is phenolic hydroxyl protecting group selected from a group consisting of benzyl group, tetrahydropyrane, acetyl group, and tert-butyl; The above listed are some of the fine protecting groups, and there are many other group can be used for protection. As benzyl group is more convenient for deprotection, R is preferably benzyl group in this invention; the synthetic route is:

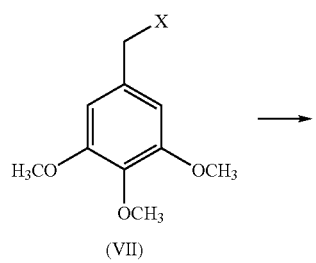

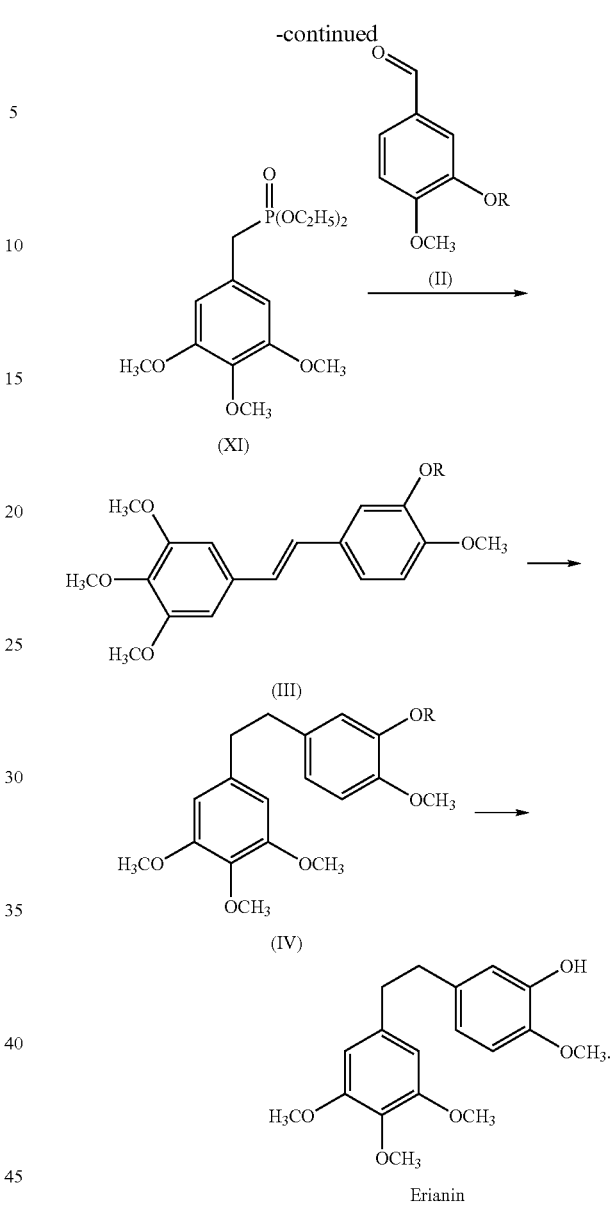

In one preferred embodiment of this invention, 3,4,5-trimethoxyl toluene was brominated with N-bromo-succinimide (NBS) and benzoylperoxide (BPO) in inert solvent such as carbon tetrachloride, and 3,4,5-trimethoxyl benzyl bromide was obtained.

In step B1,

Triethyl phosphate can be superseded by other phosphours agents, such as phosphonate, phosphorous ester, phosphine oxide, or phosphoamide, making similar reaction to synthesize Erianin.

In one preferred example of this invention, stirring 3,4,5-trimethoxyl benzyl bromide (VII) and triethyl phosphorous in toluene for refluxing reaction 10~14 hours, slightly cooling it down, distilling under reduced pressure to remove toluene and triethyl phosphate and the liquid product was obtained (XI).

In step B2,

Wherein said inert solvent was selected from at least one of dioxane, tetrahydrofuran, dimethylformamide, dimethyl sulphoxide, acetonitrile, hexamethyl phosphoramide or tetrachlormethane, and tetrahydrofuran is preferred.

Wherein said alkali in the reaction includes all kinds of organic alkali and inorganic alkali, organic alkali is preferred, such as potassium t-butoxide, diisopropylethylamine, triethylamine, or diisopropylethylamine. Potassium t-butoxide was the alkali used in one preferred example of the invention.

In one preferred example of this invention, compound (XI) and isovanillin protected by benzyl group (II) were reacted in tetrahydrofuran with potassium t-butoxide to get compound (III), which through washing, drying, concentrating and recrystallizing for further use.

In the step B3,

Wherein said organic solvent is selected from at least one of esters organic solvent or alcohols organic solvent, the mixture of ethyl acetate and ethanol being preferred. Wherein said hydrogenation catalyst is selected from at least one of palladium or nickel series, such as Pd—C catalyst and Ni—Al catalyst. Pd—C catalyst was the preferred hydrogenation catalyst in one preferred example of the invention.

In the step B4,

R is benzyl group as preferred, and the protecting group can be removed during the hydrogenation reaction in step A2. The protecting group can be removed by the common practice in the field to obtain the final product Erianin if other phenolic hydroxyl protecting group such as tetrahydropyrane is used.

The following description of the preferred embodiments of this invention with drawings is to expound in detail but not to constraint the invention.

BRIEF DESCRIPTION OF THE DRAWINGS

FIG. 4~FIG. 6 are the mass spectra of Erianin, the final product prepared according to this invention.

DESCRIPTION OF THE PREFERRED EMBODIMENTS

Figure 1:
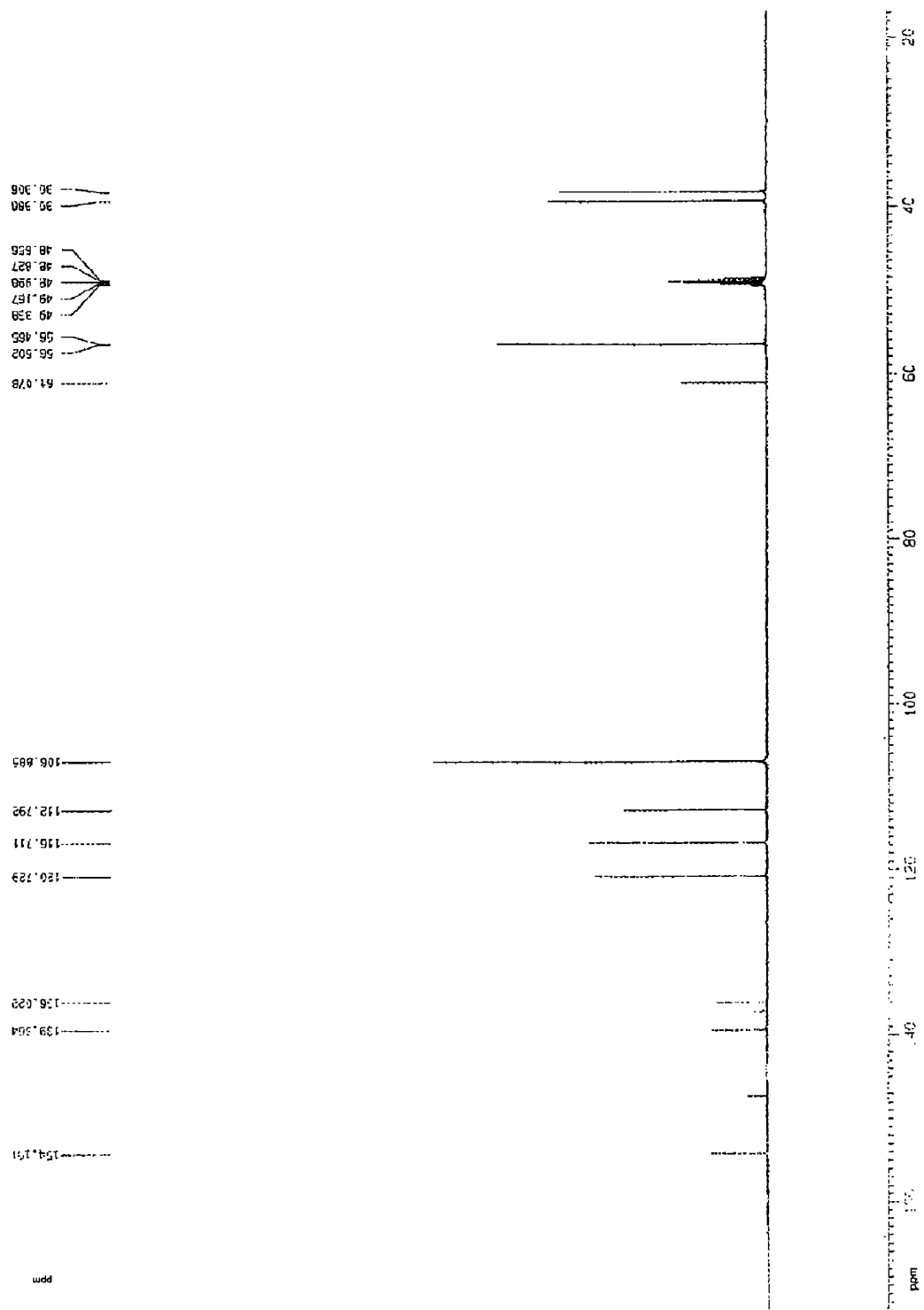
FIG. 1 is the nuclear magnetic resonance spectra (C) of Erianin, the final product prepared according to this invention.

All the starting materials and reagents used in this invention, unless otherwise specified, were purchased from market.

Example 1

Chemical Synthesis of Erianin

Step 1. Preparation of 3,4,5-trimethoxyl benzyl alcohol

Adding 3,4,5-trimethoxybenzaldehyde (15 g, 76.45 mmol) and anhydrous alcohol (200 ml) in the three-necked bottle (250 ml), heating to 40° C. to dissolve, adding sodium borohydride (1.48 g, 38.23 mmol), heating to reflux for 45 minutes, and monitored by TLC. When the reaction is completed, cooling it to room temperature, adding deionized water (10 ml, 555.8 mol), to quench the reaction and suction filtering, washing the filter residue by anhydrous alcohol (20 ml), conflating the filtrate, concentrating in rotarory evaporater to dry, adding dichlormethane (100 ml) to dissolve, washing with sodium hydroxide solution (50 ml) twice and with deionized water (50 ml) twice, adding proper amount of anhydrous magnesium sulfate to dry overnight, filtering, washing the filter residue with dichlormethane (20 ml), conflating the filtrate, concentrating in rotarory evaporater to dry to get 3,4,5-trimethoxyl benzyl alcohol, 14.05 g of colorless oily product), the yield: 92.72%.

The product does not need to be further purified for following reaction. If pure product is wanted, it can be vacuum distilled for the fraction of distillate of BP 216-218° C./12 mmHg.

Step 2. Preparation of 3,4,5-trimethoxyl benzyl bromide

Dissolving 3,4,5-trimethoxyl benzyl alcohol (14.05 g, 70.89 mmol) in dichlormethane (100 ml) in a three-necked bottle (250 ml); dissolving phosphorus tribromide (6.73 ml, 70.89 mmol) in dichlormethane (25 ml) for it to react at room temperature for 50 minutes, cooling in refrigeratory, slowly adding deionized water (18 ml, 1.0 mol) dropwise to quench, washing with deionized water (100 ml) twice, drying with anhydrous magnesium sulfate, filtering, washing the filter residue with dichlormethane (20 ml), conflating the filtrate, concentrating in rotarory evaporater, and vacuum drying to get 3,4,5-trimethoxyl benzyl bromine (16.05 g of faint yellow solid), yield: 84.44%.

The product does not need to be further purified for following reaction. If pure product is wanted, it can be recrystallized to get the white lamellar crystal with a 1:3 mixture of ethyl acetate and n-hexane.

Step 3. Preparation of 3,4,5-trimethoxyl benzyl triphenylphosphine bromide

Dissolving 3,4,5-trimethoxyl benzyl bromide (16.05 g, 61.47 mmol) in toluene (150 ml) in a three-necked bottle (250 ml), adding triphenylphosphine (16.12 g, 61.47 mmol) and dissolving immediately, heating to reflux for 1 hour, white solid being separated, cooling to room temperature, suction filtering, and washing the filter cake with toluene (30 ml). After vacuum drying, 3,4,5-trimethoxyl benzyl triphenylphosphine bromide (27.81 g of white powder solid) was isolated, yield: 86.44%.

The product does not need to be further purified for following reaction. If pure product is needed, it can be washed with acetone to get white powder solid.

Step 4. Preparation of isovanillin protected by benzyl group

Adding isovanillin (15 g, 98.59 mmol) to anhydrous alcohol (200 ml) in a three-necked bottle (250 ml), heating to dissolve at 40° C., adding potassium carbonate (9 g, 65.07 mmol), adding benzylchloride (15 ml, 130.13 mmol) when stirring, and heating to reflux for 1 hour; After the completion of the reaction (monitored by TLC), cooling it down to 50° C., filtering while hot, cooling the filtrate in refrigeratory overnight, crystal was precipitated, suction filtering, and washing the filter cake with toluene (30 ml). After vacuum drying, isovanillin protected by benzyl group (white acicular crystal, 19.72 g) was isolated, yield: 82.56%.

The product does not need to be further purified for following reaction. If pure product is needed, it can be recrystallized by absolute alcohol to get white styloid solid.

Step 5. Preparation of Cis/Trans Product

Adding 3,4,5-trimethoxyl benzyl triphenylphosphine bromide (20.00 g, 38.21 mmol) and tetrahydrofuran (150 ml) in a three-necked bottle (250 ml), stirring the suspension, dissolving isovanillin protected by benzyl group (10.00 g, 41.27 mmol) in tetrahydrofuran (70 ml), and adding it to a dropping funnel (100 ml); adding solid potassium t-butoxide (7.46 g, 66.49 mmol) to the reaction bottle, when the reaction system turning to sanguine, stirring for 5 minutes at room temperature, slowly adding the solution of isovanillin protected by benzyl group dropwise, and stirring for 20 minutes at room temperature again; After the completion of the reaction (monitored by TLC), putting the reaction mixture into a separating funnel (500 ml), adding deionized water (140 ml), the solution being stratified, extracting with diethyl ether (300 ml) twice, collecting the layer in diethyl ether, drying with anhydrous magnesium sulfate, filtering, and washing the filter cake with diethyl ether (50 ml); concentrating the filtrate in rotarory evaporater to dry to get oily product (25 g); adding absolute alcohol to solidify and suction filtering to get a faint yellow solid (12.50 g), yield: 84.44%.

Step 6. Recrystallisation of the cis/trans Product

Adding cis/trans product (12.50 g, 30.75 mmol) and anhydrous alcohol (20 ml) in a round bottom flask (50 ml), heating till some solid is dissolved, stirring at room temperature, suction filtering, washing the filter cake with dry ether (10 ml), and drying by Infrared lamp to get pure cis/trans product (9.27 g) in faint yellow powder, yield: 74.16%.

Step 7. Preparation of Erianin

Dissolving pure cis/trans product (5.14 g, 12.56 mmol) in the mixture of ethyl acetate (100 ml) and absolute alcohol (60 ml) in a three-necked bottle (250 ml), the solution being faint yellow, adding 5% Pd—C (0.5 g), stirring while passing hydrogen into the mixture, stirring for 1 hour at room temperature, filtering, the filtrate being colorless, and concentrating it in rotarory evaporater to dry to get the oily product (4.05 g), the crude product of Erianin, yield: 100%.

Step 8. Purification of Erianin

Dissolving the crude product of Erianin in anhydrous alcohol (20 ml) in a round bottom flask (50 ml), filtering the insoluble substance (if any), and leaving it in stillness for white crystal to be separated at room temperature, standing overnight. When the solvent is completely volatilized, a great quantity of white crystal is separated. Suction filtering and washing the filter cake with alcohol to get white crystal (3.56 g), yield: 100%.

Figure 2:
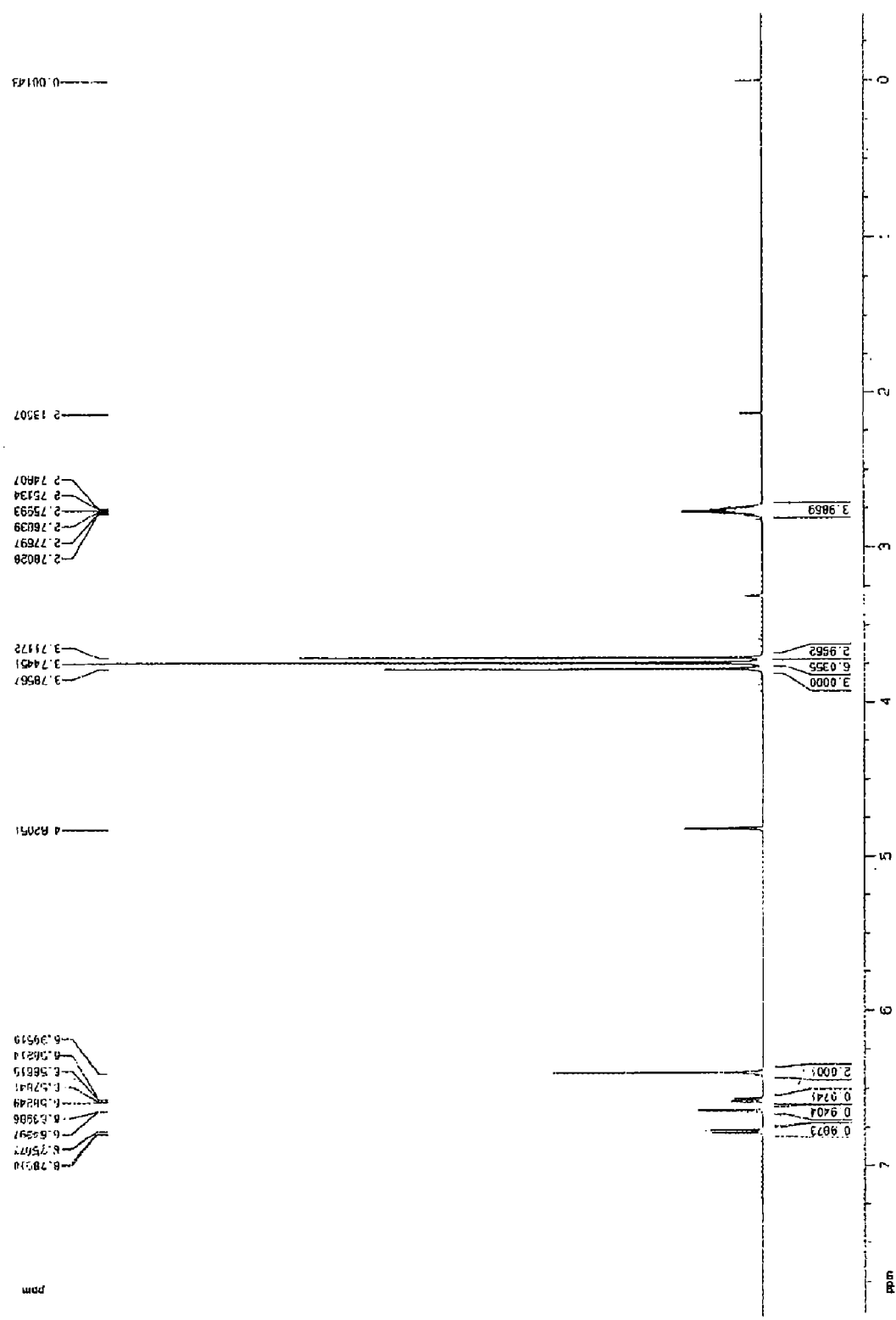
FIG. 2 is the nuclear magnetic resonance spectra (H) of Erianin, the final product prepared according to this invention.
Figure 3:
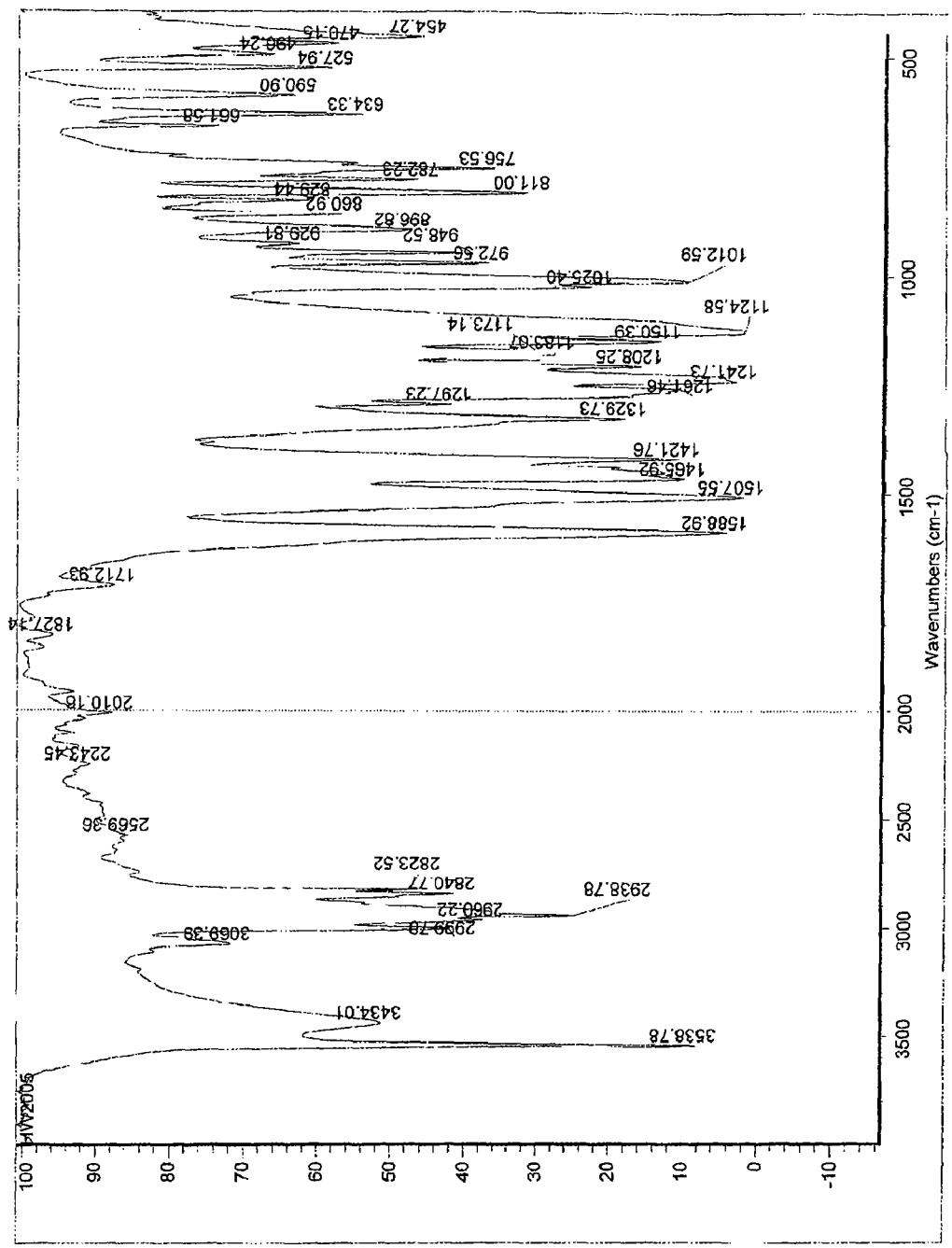
FIG. 3 is the Infrared spectra of Erianin, the final product prepared according to this invention.
Figure 4:
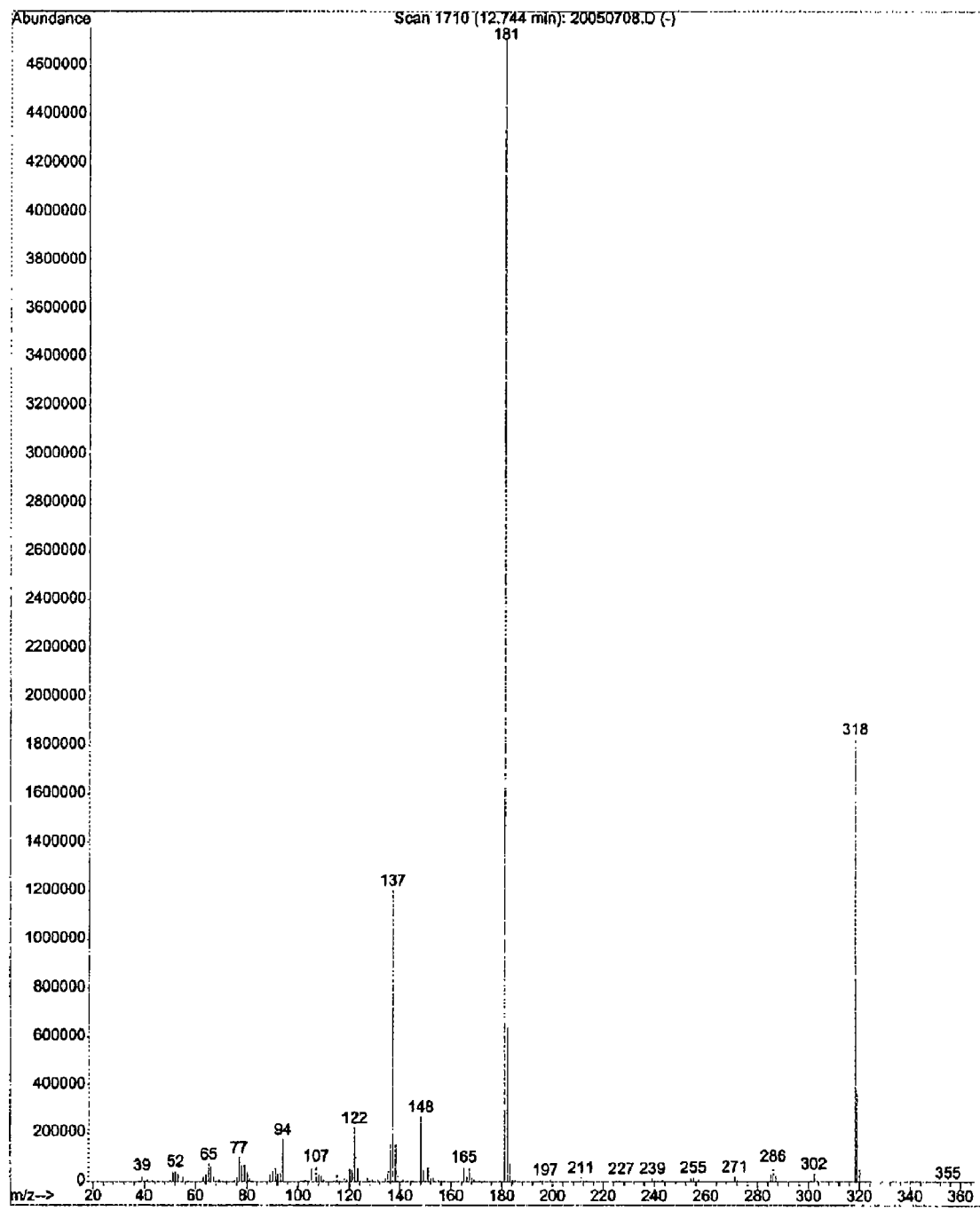
Figure 6:
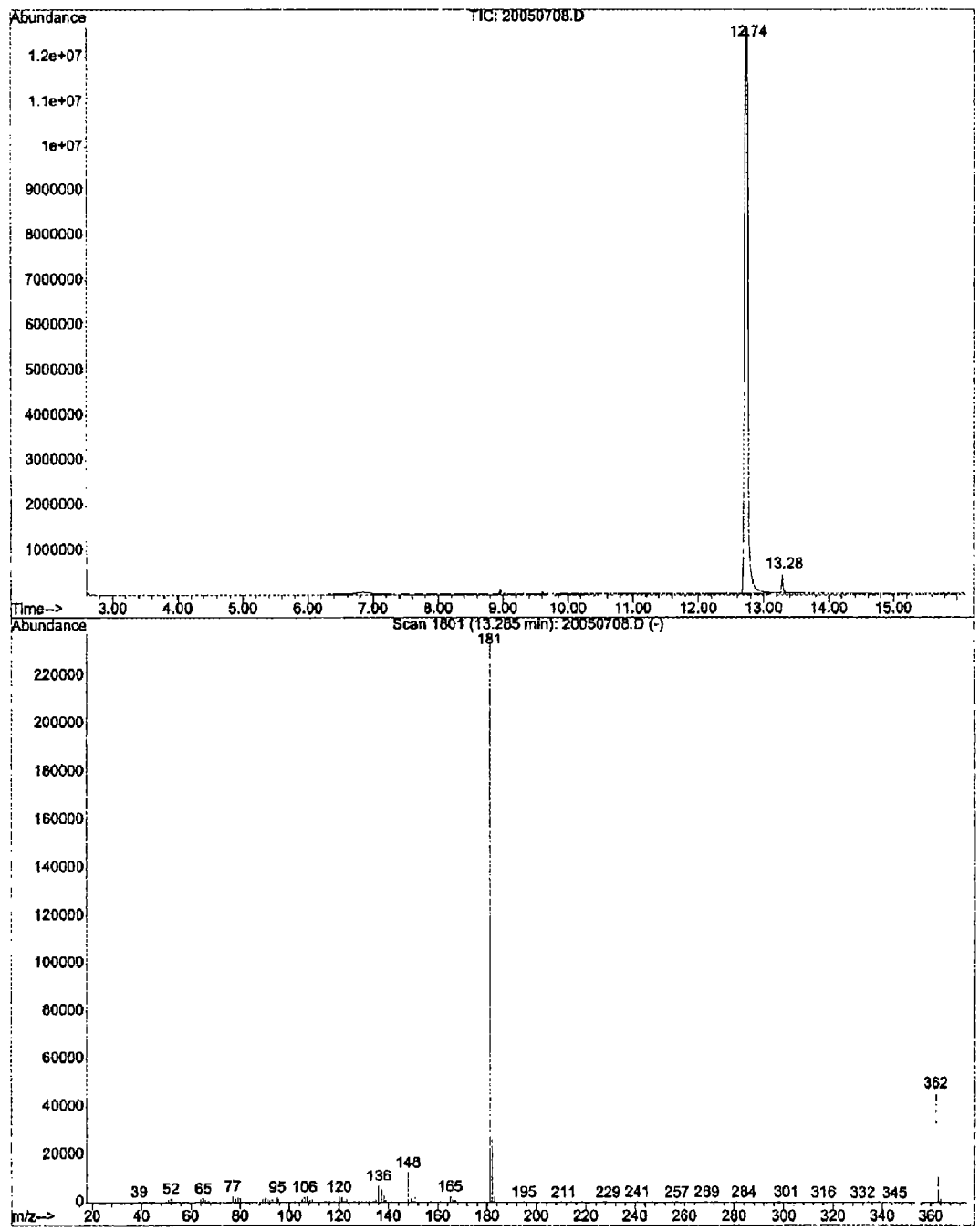

The result of Erianin's physical property test is:
(1) melting point: 76-77° C.
(2) NMR analysis:
    Equipment: Avance DMX500; dissolvent: deuterium methanol, the result in FIG. 1 and FIG. 2
(3) IR analysis:
    Equipment: Nicolet E.S.P560, the result in FIG. 3.
(4) MS analysis:
    Equipment: HP6890/5973 GC/MS united equipment, the result in FIG. 4~FIG. 6.

The above results show that the final product of present invention is Erianin.

Example 2

Synthesis of Erianin

Step 1. Bromination of 3,4,5-trimethoxyl toluene

Adding 3,4,5-trimethoxyl toluene (10 mmol) in a 50 ml three-mouth flask, adding carbon tetrachloride (20 ml), heating in oil bath while stirring at 82~84° C., for refluxing; then adding the mixture of N-bromosuccinimide (NBS, 10 mmol) and benzoylperoxide (BPO, 0.5 mmol) in batches for about 10 minustes, continuing stirring for 20 minustes, and filtering; Then washing the filtrate with water and saturated sodium chloride solution, drying it with anhydrous magnesium sulfate, filtering, evaporating to dry and passing a Column, and collecting the component having the maximum polarity to have 3,4,5-trimethoxyl benzyl bromide.

Step 2. Reaction with triethyl phosphorous

Stirring 3,4,5-trimethoxyl benzyl bromide (10 mmol), triethyl phosphate (50 mmol) and toluene (40 ml) for refluxing 12 hours, and distilling under reduced pressure after cooling down slightly to remove toluene and triethyl phosphate (10~20 mmHg/80° C.) and to obtain the liquid product (XI).

Step 3. Bonding Reaction 3.1 Benzyl group protection of isovanillin
Mixing isovanillin (6.6 mmol), benzyl-chloride (13.9 mmol), anhydrous potassium carbonate (4.7 mmol) and alcohol (15 ml) and stirring for refluxing 5 hours, concentrating when the reaction is completed, redissolving in dichlorethane (10 ml), and washing with 5% sodium hydroxide (10 ml) three times; then washing the organic layer with saturated sodium chloride solution (10 ml) and water (10 ml) twice, and finally drying by anhydrous sodium sulfate; concentrating the filtrate to get the product; the product was recrystallized in methanol or dichlormethane.

3.2 Reaction of isovanillin Protected by Benzyl Group
Heating the product of step 2 (10 mmol), isovanillin protected by benzyl group (10 mmol), and tetrahydrofuran (THF, 30 ml) to reflux with stirring, adding potassium t-butoxide (t-BuOK, 12 mmol) in batches to avoid acute boiling, and continue to react for another 1 hr; Dissolving the reaction product with diethyl ether (40 mmol) (small amount of dichlormethane can be added if dissolution is not complete), washing with water and saturate sodium chloride, drying by anhydrous sodium sulfate, and concentrating the filtrate to get yellow product. The product can be recrystallized with n-hexane or ethyl acetate.

Step 4. Hydrogenation Reaction

Stirring the product (1.0 g) of the bonding reaction, 5% Pd—C catalyst (0.25 g) and alcohol (100 ml) in oil bath (70~75° C.) while passing hydrogen into the mixture for 1 hour, filtering, and concentrating the filtrate to get yellow viscous liquid. After the purification by column chromatography a white solid product was obtained, Erianin.

APPLICATION IN INDUSTRY

The present invention is the first time to synthesize Erianin by synthetic method. The starting material is easy to get and the agent is cheaper, the operation is simple and secure, the yield rate is high, and it is fitting for industrial mass production.

The description in the preferred embodiments above does not constraint the invention. Those skilled in the field can make various kinds of changes and modifications according to this invention, all of which would belong to the limit of the claims of this invention, unless they break away from the spirit of the invention.

What is claimed is:

1. A process for preparing Erianin, comprising the steps of:
   A1. reacting compound of general formula (I) with compound of general formula (II) by bonding reaction in inert solvent which contains alkali to form compound of general formula (III);
   A2. reacting compound (III) obtained in step A1 with hydrogen by hydrogenation reaction to form compound of general formula (IV) in organic solvent, with hydrogenation catalyst; and
   A3. removing the hydroxyl protecting group R of compound (IV) obtained in step A2 by hydroxy group deprotection reaction to form Erianin;
Wherein,
   X is halogen selected from a group consisting of Cl, Br, or I;
   in step A1, said alkali is potassium t-butoxide;
   R is benzyl group, and when R is benzyl group, the protecting group is removed during hydrogenation reaction in step A2;
   the synthetic route is:

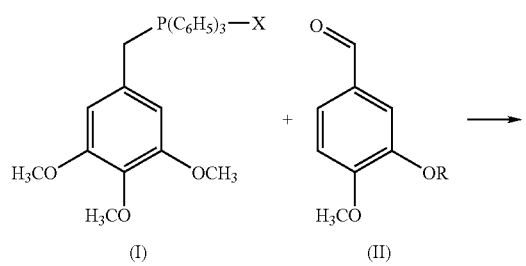

(I)    (II)

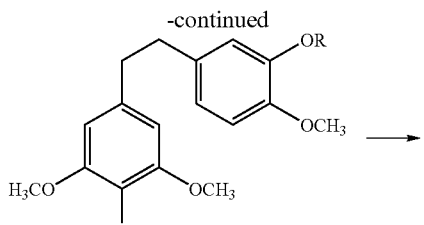

(IV)

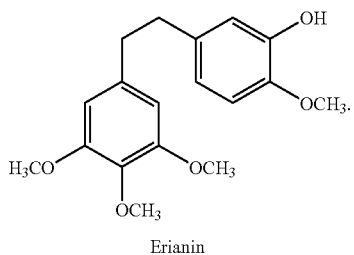

Erianin

2. The process of claim 1, wherein in step A1, said inert solvent is one or more than one kinds of solvent selected from a group consisting of dioxane, tetrahydrofuran, dimethylformamide, dimethyl sulphoxide, acetonitrile, hexamethyl phosphoramide and tetrachloromethane.

3. The process of claim 2, wherein the inert solvent is tetrahydrofuran.

4. The process of claim 1, wherein in step A2, the organic solvent is one or more than one kinds of solvent selected from a group consisting of esters organic solvent and alcohols organic solvent; and
   the hydrogenation catalyst is one or more kinds of catalyst selected from a group consisting of palladium or nickel series.

5. The process of claim 4, wherein the organic solvent is a mixed solvent of ethyl acetate and ethanol; and the said hydrogenation catalyst is Pd—C catalyst.

6. The process of claim 1, wherein compound (I) is prepared from 3,4,5-trimethoxybenzaldehyde or 3,4,5-trimethoxyl toluene.

7. The process of claim 6, comprising following steps:
   a. preparing compound (VI) from compound (V) in the presence of a reducing agent;
   b. reacting compound (VI) with halide to form compound (VII); and
   c. reacting compound (VII) with triphenylphosphine to form compound (I);
the synthetic route is:

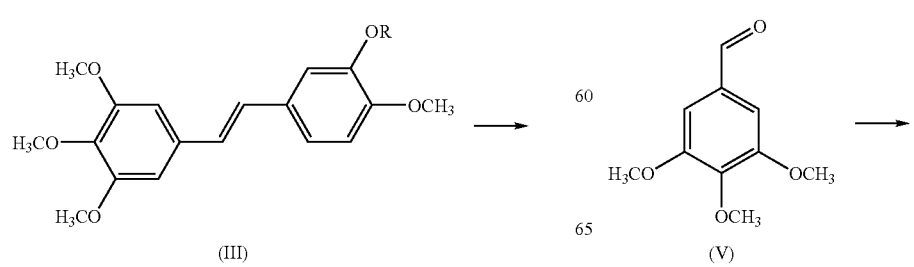

(III)    (V)

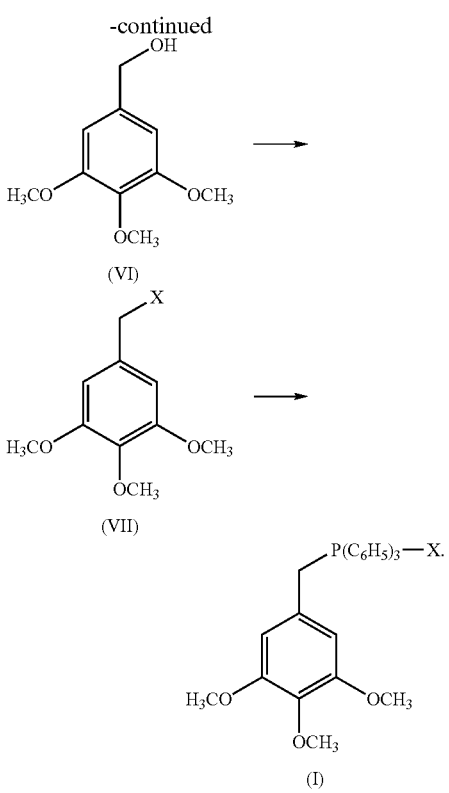

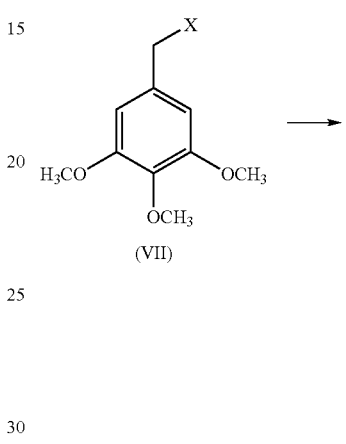

8. The process of claim 1, wherein when R is benzyl group, reacting isovanillin (VIII) with benzyl chloride to form compound (X); and
   the reaction equation is:

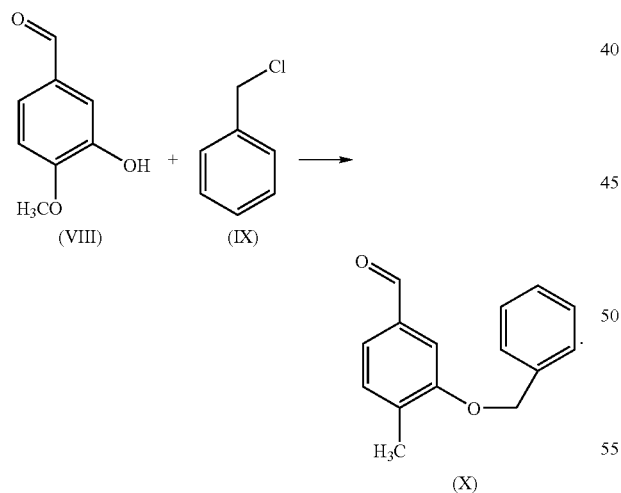

9. A process for preparing Erianin, comprising the steps of:
B1. reacting compound (VII) with triethyl phosphite in the aromatic organic solvent to form compound (XI);
B2. reacting compound (XI) with compound (II) in the inert solvent which contains alkali to form compound (III); and
B3. reacting compound (III) with hydrogen by hydrogenation reaction to form compound (IV) in the organic solvent, with hydrogenation catalyst;

B4. removing the hydroxyl protecting group R of compound (IV) obtained in step B3 to form Erianin;
wherein,
X is a halogen selected from a group consisting of Cl, Br, and I;
in step B2, the said alkali is potassium t-butoxide;
R is a benzyl group, and when R is a benzyl group, the protecting group is removed during hydrogenation reaction in step B3;
the synthetic route is:

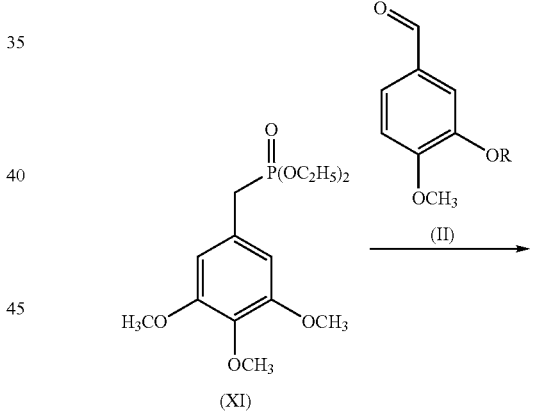

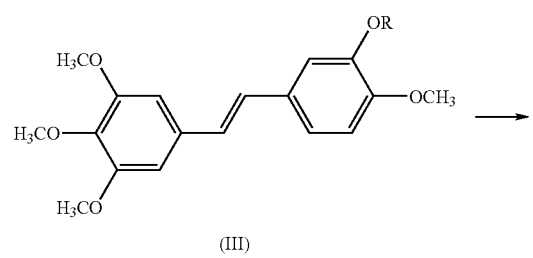

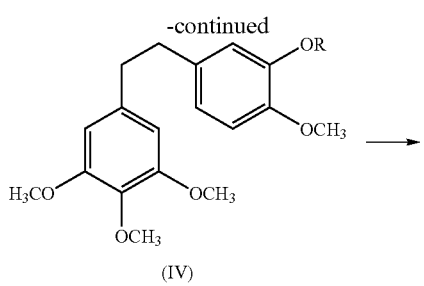
(IV)

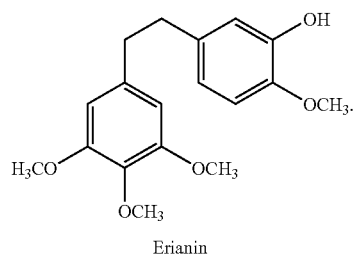
Erianin

10. The process of claim 9, wherein in step B2, the said inert solvent is one or more kinds of solvent selected from a group consisting of dioxane, tetrahydrofuran, dimethylformamide, dimethyl sulphoxide, acetonitrile, hexamethyl phosphoramide and tetrachloromethane;

in step B3, said organic solvent is one or more kinds of solvent selected from a group consisting of esters organic solvent or alcohols organic solvent; and said hydrogenation catalyst is one or more kinds of catalyst selected from a group consisting of palladium or nickel series.

11. The process of claim 10, wherein in step B3, the organic solvent is the mixture of ethyl acetate and ethanol; and the hydrogenation catalyst is Pd—C catalyst.

* * * * *